(12) United States Patent
Buffat et al.

(10) Patent No.: US 7,691,857 B2
(45) Date of Patent: Apr. 6, 2010

(54) MUSCARINIC AGENTS AS THERAPEUTIC COMPOUNDS

(75) Inventors: Maxime Buffat, Cardiff (GB); James Eric Thomas, Cardiff (GB); Harvard Robin Davies, Cardiff (GB)

(73) Assignee: Muscagen Limited, Cardiff (GB)

( * ) Notice: Subject to any disclaimer, the term of this patent is extended or adjusted under 35 U.S.C. 154(b) by 285 days.

(21) Appl. No.: 10/581,833

(22) PCT Filed: Dec. 6, 2004

(86) PCT No.: PCT/GB2004/005096

§ 371 (c)(1),
(2), (4) Date: Apr. 13, 2007

(87) PCT Pub. No.: WO2005/054242

PCT Pub. Date: Jun. 16, 2005

(65) Prior Publication Data

US 2008/0039469 A1  Feb. 14, 2008

(30) Foreign Application Priority Data

Dec. 5, 2003  (GB) ................... 0328295.1

(51) Int. Cl.
- *A61K 31/437* (2006.01)
- *A61K 31/4985* (2006.01)
- *A61P 25/28* (2006.01)
- *C07D 471/04* (2006.01)
- *C07D 487/04* (2006.01)
- *C07D 498/04* (2006.01)

(52) U.S. Cl. ............. 514/249; 514/300; 514/302; 514/303; 546/113; 546/116; 546/118; 544/350

(58) Field of Classification Search ........... 546/116, 546/113, 118; 514/302, 249, 300, 303; 544/350
See application file for complete search history.

(56) References Cited

OTHER PUBLICATIONS

Lohse et al., Perkin 1 (2000), (5), 659-665.*

Jensen et al., Chemistry—A European Journal (2002), 8(5), 1218-1226.*

Taverni et al., Brain injury: [BI], (Jan. 1998) vol. 12, No. 1, pp. 77-80.*

* cited by examiner

*Primary Examiner*—D. Margaret Seaman
*Assistant Examiner*—Niloofar Rahmani
(74) *Attorney, Agent, or Firm*—Husch Blackwell Sanders Welsh & Katz

(57) ABSTRACT

Muscarinic agonists of the formula (I) with M1 selectivity which are useful as agents for stimulating the cognitive functions of the brain.

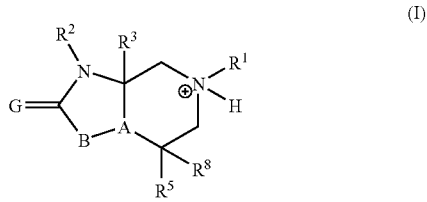

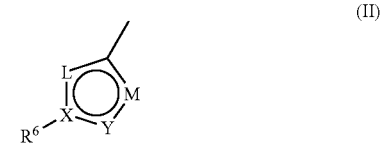

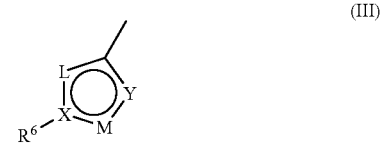

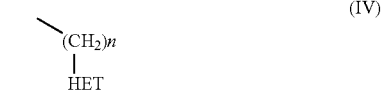

15 Claims, No Drawings

MUSCARINIC AGENTS AS THERAPEUTIC COMPOUNDS

FIELD OF THE INVENTION

This invention relates to muscarinic agonists with $M_1$ selectivity which are useful as agents for stimulating the cognitive functions of the brain.

BRIEF DESCRIPTION OF THE INVENTION

According to a first embodiment of the present invention, there is provided a compound of the formula:

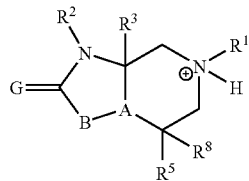

or a pharmaceutically acceptable salt thereof, wherein:

A is CH or nitrogen;

B is —$CH_2$—, —CHF—, —$CF_2$—, $NR_4$ or O, with the proviso that when A is N, B is —$CH_2$—, —CHF— or —$CF_2$—;

G is oxygen or =N—CN, $R_1$ is hydrogen or $C_{1-6}$ alkyl;

$R_2$ is hydrogen; $C_{1-10}$ alkyl optionally substituted with $C_{1-6}$ alkoxy or halogen; aralkyl, a —$CH_2$-heterocycle or a —$CH_2$—$C_5$ cycloalkyl ring each of which may be optionally substituted with one or more of halo, hydroxy, $C_{1-6}$ alkyl, $C_{1-6}$ haloalkyl, $C_{1-8}$ alkoxy, $C_{1-6}$ haloalkoxy, $C_{2-6}$ alkenyl, $C_{2-6}$ haloalkenyl, $C_{2-6}$ alkynyl or $C_{2-6}$ haloalkynyl;

$R_3$ is hydrogen; a cyclic alkyl radical containing from 3-6 carbon atoms or a $C_1$-$C_6$ alkyl;

$R_4$ is hydrogen or lower alkyl;

$R_5$ is a 5-membered unsaturated heterocyclic ring having one of the following structures:

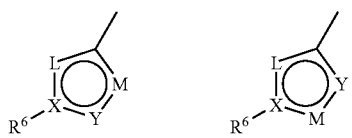

where L and M are independently O or N (or NH where the circumstances require) with the proviso that both of L and M cannot be O; Y is S, CH, O or N (or NH where the circumstances require); X is C or N; and $R_6$ is lower alkyl; hydrogen; arylamino optionally substituted with one or more of halo, hydroxy, $C_{1-6}$ alkyl, $C_{1-6}$ haloalkyl, $C_{1-6}$ alkoxy, $C_{1-6}$ haloalkoxy, $C_{2-6}$ alkenyl, $C_{2-6}$ haloalkenyl, $C_{2-6}$ alkynyl or $C_{2-6}$ haloalkynyl; aralkyl optionally substituted with one or more of halo, hydroxy, $C_{1-6}$ alkyl, $C_{1-6}$ haloalkyl, $C_{1-6}$ alkoxy, $C_{1-6}$ haloalkoxy, $C_{2-6}$ alkenyl, $C_{2-6}$ haloalkenyl, $C_{2-6}$ alkynyl or $C_{2-6}$ haloalkynyl; or a group of formula:

wherein n is an integer in the range from 1 to 4 and HET is a heterocyclic group optionally substituted with one or more of halo, hydroxy, $C_{1-6}$ alkyl, $C_{1-6}$ haloalkyl, $C_{1-6}$ alkoxy, $C_{1-6}$ haloalkoxy, $C_{2-6}$ alkenyl, $C_{2-6}$ haloalkenyl, $C_{2-6}$ alkynyl or $C_{2-6}$ haloalkynyl;

or $R_5$ may also be $C_2$-$C_4$-aralkyl (e.g. $CH_2$—$CH_2$-phenyl), —$CH_2$—O—$R_7$ where $R_7$ is $C_{1-6}$ alkyl, $C_{2-6}$ alkenyl, $C_{2-6}$ alkynyl, $C_2$-$C_4$ aralkyl (e.g. $CH_2$—$CH_2$-phenyl) which groups may be optionally substituted with fluoro or hydroxy; and $R_8$ is hydrogen or aryl (optionally substituted with one or more of halo, hydroxy, $C_{1-6}$ alkyl, $C_{1-6}$ haloalkyl, $C_{1-6}$ alkoxy, $C_{1-6}$ haloalkoxy, $C_{2-6}$ alkenyl, $C_{2-6}$ haloalkenyl, $C_{2-6}$ alkynyl or $C_{2-6}$ haloalkynyl);

with the proviso that when either $R_3$ or $R_8$ is not hydrogen, the other is hydrogen.

In accordance with a second embodiment of the invention, there is provided a pharmaceutical composition comprising a therapeutically effective amount of the compound of the first embodiment.

In accordance with a third embodiment of the invention, there is provided a compound in accordance with the first embodiment of the invention for use as a medicament.

In accordance with a fourth embodiment of the invention, there is provided the use of a compound in accordance with the first embodiment of the invention in the manufacture of a medicament for the treatment of disorders caused by the malfunction of the acetylcholine or muscarinic systems.

In accordance with a fifth embodiment of the invention, there is provided a method for the treatment, prophylaxis and/or inhibition of disorders caused by the malfunction of the acetylcholine or muscarinic systems comprising the administration of a therapeutically effective amount of a compound in accordance with the first embodiment of the invention to a subject in need thereof.

DETAILED DESCRIPTION OF THE INVENTION

In the embodiments of the invention,

G is preferably oxygen.

$R_1$ is preferably hydrogen or lower alkyl such as methyl. $R_1$ is most preferably hydrogen.

$R_2$ may be $C_{1-8}$ alkyl, such as n-$C_5H_{11}$, or —$CH_2$-aryl, preferably —$CH_2$—$C_6H_5$ in which the aryl may be unsubstituted or substituted with one or more of halo, hydroxy, $C_{1-6}$ alkyl, $C_{1-6}$ haloalkyl, $C_{1-6}$ alkoxy, $C_{1-6}$ haloalkoxy, $C_{2-6}$ alkenyl, $C_{2-6}$ haloalkenyl, $C_{2-6}$ alkynyl or $C_{2-6}$ haloalkynyl. Alternatively, $R_2$ may be —$CH_2$—$C_5$ cycloalkyl such as —$CH_2$-cyclopentane or —$CH_2$-cyclopenta-1,3-diene. Another preferred $R_2$ radical is —$CH_2$-heterocyclic aryl, for example —$CH_2$-benzoxazole, in which the —$CH_2$-heterocyclic aryl may be optionally substituted with one or more of halo, hydroxy, $C_{1-6}$ alkyl, $C_{1-6}$ haloalkyl, $C_{1-6}$ alkoxy, $C_{1-6}$ haloalkoxy, $C_{2-6}$ alkenyl, $C_{2-6}$ haloalkenyl, $C_{2-6}$ alkynyl or $C_{2-6}$ haloalkynyl. The invention includes within its scope other —$CH_2$-heterocyclic aryl groups such as —$CH_2$-benzodioxole, —$CH_2$-benzooxathiole, —$CH_2$-benzoimidazole, —$CH_2$-benzothiazole, —$CH_2$-benzodithiole —$CH_2$-pyridyl, —CH$_2$-pyrimidyl all of which may be optionally substituted with one or more of halo, hydroxy, C$_{1-6}$ alkyl, C$_{1-6}$ haloalkyl, C$_{1-6}$ alkoxy, C$_{1-6}$ haloalkoxy, C$_{2-6}$ alkenyl, C$_{2-6}$ haloalkenyl, C$_{2-6}$ alkynyl or C$_{2-6}$ haloalkynyl. The invention also includes within its scope other non-aromatic —CH$_2$-heterocyclic groups such as —CH$_2$-thiophene, —CH$_2$-furan, —CH$_2$-pyrrolidine, —CH$_2$-oxathiolane, —CH$_2$-thiazolidine, —CH$_2$-oxazolidine, —CH$_2$-dithiolane, —CH$_2$-dioxolane, —CH$_2$-imidazoline all of which may be optionally substituted with one or more of halo, hydroxy, C$_{1-6}$ alkyl, C$_{1-6}$ haloalkyl, C$_{1-6}$ alkoxy, C$_{1-6}$ haloalkoxy, C$_{2-6}$ alkenyl, C$_{2-6}$ haloalkenyl, C$_{2-6}$ alkynyl or C$_{2-6}$ haloalkynyl.

Also in accordance with the present invention but presently less preferred is —CH$_2$-naphthyl in which the naphthyl is unsubstituted or substituted with one or more of halo, hydroxy, C$_{1-6}$ alkyl, C$_{1-6}$ haloalkyl, C$_{1-6}$ alkoxy, C$_{1-6}$ haloalkoxy, C$_{2-6}$ alkenyl, C$_{2-6}$ haloalkenyl, C$_{2-6}$ alkynyl or C$_{2-6}$ haloalkynyl.

R$_3$ is preferably hydrogen, cyclobutyl, cyclopropyl, methyl, ethyl, isopropyl, butyl, sec-butyl, more preferably hydrogen or cyclobutyl.

R$_4$ is preferably hydrogen.

R$_5$ is preferably one of the following 5-membered unsaturated heterocyclic ring structures:

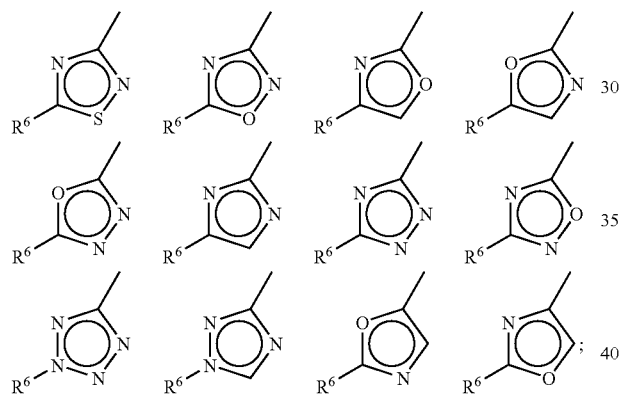

where R$_6$ is preferably methyl, aralkyl, arylamino, aralkyl substituted by one or more halo and having a methylene group linking the aryl to the unsaturated 5-membered ring, aralkyl substituted by one or more halo and having an ethylene group linking the aryl to the unsaturated 5-membered ring, R$_6$ is more preferably phenyl, phenylamino substituted by one or more halo (e.g. chloro), phenylmethyl substituted by one or more halo (e.g chloro), or phenethyl substituted by one or more halo (e.g. chloro), R$_6$ is most preferably a meta chloro-substituted phenylamino, a meta chloro-substituted phenylmethyl or a meta chloro-substituted phenethyl.

More preferred at present amongst the above unsaturated 5 membered heterocyclic rings are:

5-methyl-1,2,4-thiadiazol-3-yl;
5-methyl-1,2,4-oxadiazol-3-yl;
5-methyl-1,4-oxazol-3-yl;
4-methyl-1,3-oxazol-2-yl;
5-methyl-1,3-oxazol-2-yl;
5-methyl-1,4-oxazol-2-yl.

When R$_5$ is —CH$_2$—O—R$_7$, R$_7$ is preferably —C$_{2-4}$-aralkyl, more preferably —CH$_2$—CH$_2$-aryl, most preferably —CH$_2$—CH$_2$-phenyl.

R$_8$ is preferably hydrogen, phenyl or halo-substituted phenyl, more preferably fluoro-substituted phenyl and most preferably 3,5-difluorophenyl.

In one aspect of the first embodiment, A is CH; B is —CH$_2$—; G is oxygen; R$_1$ is hydrogen; R$_2$ is C$_{1-10}$ alkyl, for example n-C$_5$H$_{11}$, or —CH$_2$-aryl, for example —CH$_2$—C$_6$H$_5$ (optionally substituted as described below), or —CH$_2$-heterocyclic aryl, for example —CH$_2$-benzoxazole (optionally substituted as described below). R$_3$ is cyclobutyl or H; R$_5$ is one of the preferred or more preferred 5-membered unsaturated heterocyclic ring structures specified above; and R$_8$ is H or phenyl (optionally substituted with halo). Examples of compounds falling within this definition are:

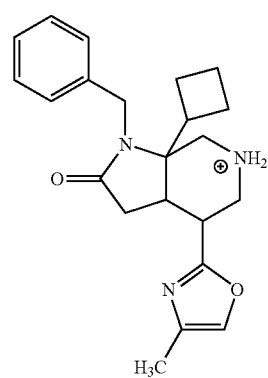

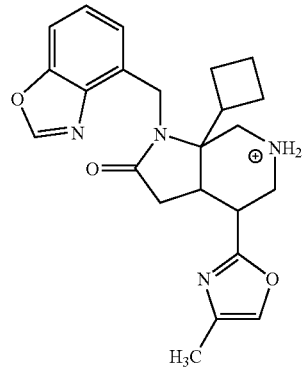

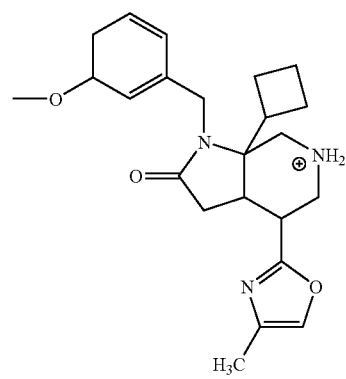

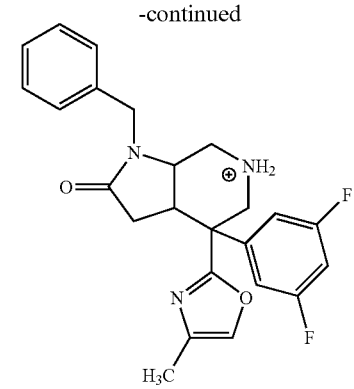

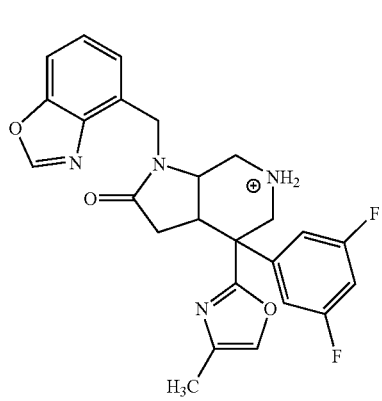

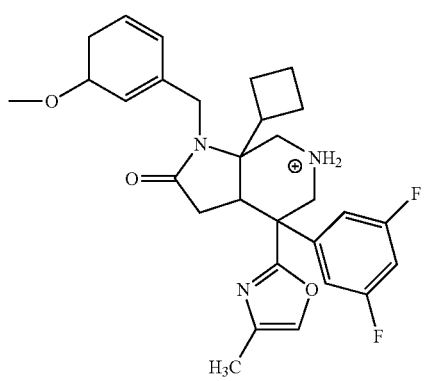

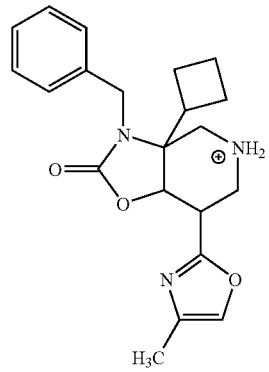

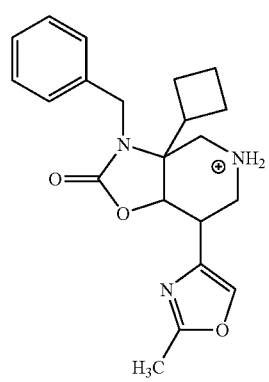

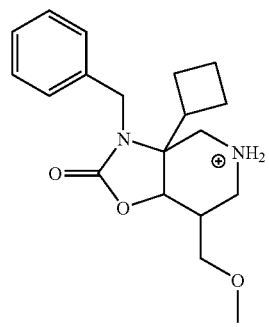

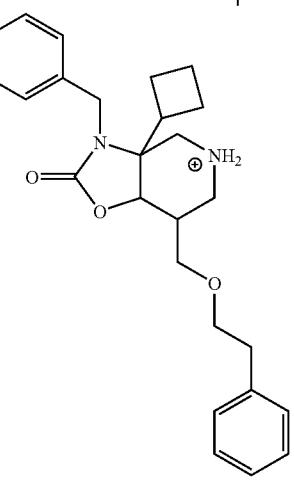

In another aspect, A is CH; B is O; G is oxygen; $R_1$ is hydrogen; $R_2$ is $C_{1-10}$ alkyl, for example n-$C_5H_{11}$, or —$CH_2$-aryl, for example. —$CH_2$—$C_6H_5$ (optionally substituted as described below), —$CH_2$—$C_{10}H_7$ (optionally substituted as described below) or —$CH_2$-heterocyclic aryl, for example —$CH_2$-benzoxazole (optionally substituted as described below). $R_3$ is cyclobutyl or H; $R_5$ is one of the preferred or more preferred 5-membered unsaturated heterocyclic ring structures specified above, —$CH_2$—O—$CH_3$ or —$CH_2$—O—$CH_2$—$CH_2$—$C_6H_5$; and $R_8$ is H or phenyl (optionally substituted with halo). Examples of compounds falling within this definition are:

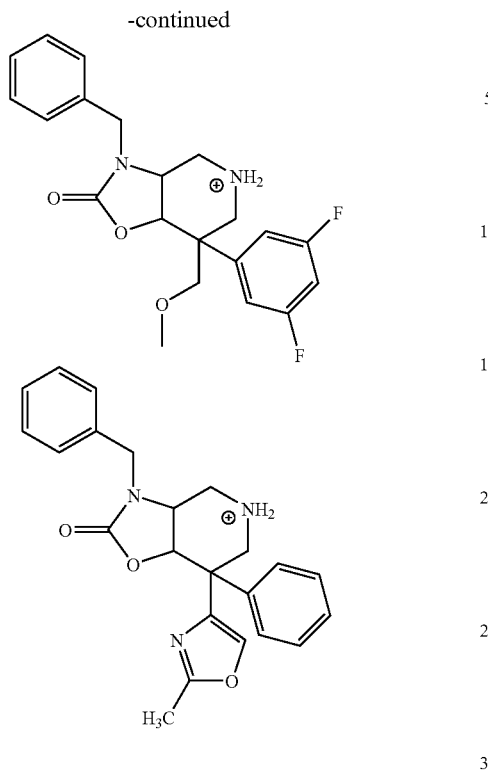

In another aspect, A is CH; B is NH; G is oxygen; $R_1$ is hydrogen; $R_2$ is $C_{1-10}$ alkyl, for example n-$C_5H_{11}$, or —$CH_2$-aryl, for example —$CH_2$—$C_6H_5$ (optionally substituted as described below), —$CH_2$—$C_{10}H_7$ (optionally substituted as described below), —$CH_2$-heterocyclic aryl, for example —$CH_2$-benzoxazole, —$CH_2$-pyridyl or —$CH_2$-pyrimidyl (optionally substituted as described below), a —$CH_2$-heterocyclic group (optionally substituted as described below), or a —$CH_2$— substituted $C_5$ cycloalkyl (optionally substituted as described above); $R_3$ is cyclobutyl or H; $R_4$ is hydrogen; $R_5$ is one of the preferred or more preferred 5-membered unsaturated heterocyclic ring structures specified above, —$CH_2$—O—$CH_3$ or —$CH_2$—O—$CH_2$—$CH_2$—$C_6H_5$; and $R_8$ is H or phenyl (optionally substituted with halo). Examples of compounds falling within this definition are:

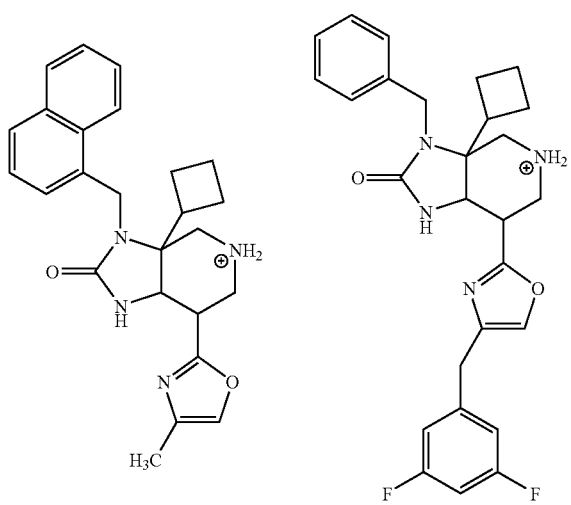

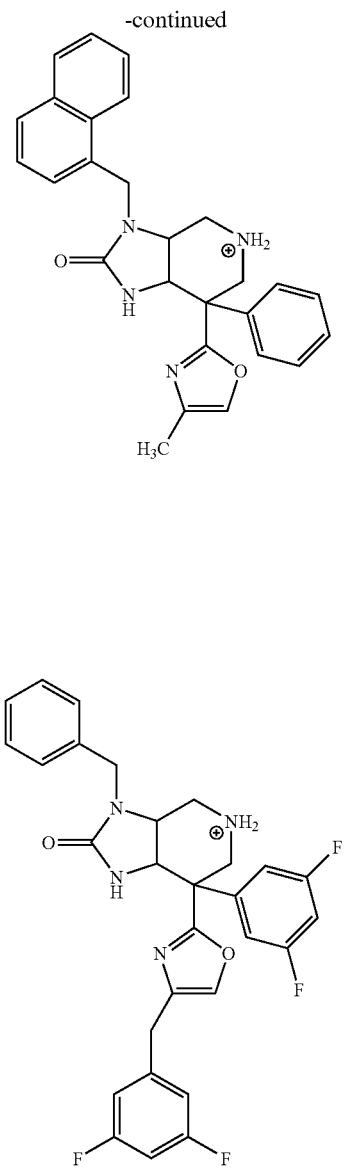

In another aspect, A is N; B is —$CH_2$—; G is oxygen; $R_1$ is hydrogen; $R_2$ is $C_{1-10}$ alkyl, for example n-$C_5H_{11}$, or —$CH_2$-aryl, for example —$CH_2C_6H_5$ (optionally substituted as described below), —$CH_2$—$C_{10}H_7$ (optionally substituted as described below) or —$CH_2$-heterocyclic aryl for example —$CH_2$-benzoxazole, $CH_2$-pyridyl or $CH_2$-pyrimidyl (optionally substituted as described below), a —$CH_2$-heterocyclic group (optionally substituted as described below), or a —$CH_2$-substituted $C_5$ cycloalkyl (optionally substituted as described above); $R_3$ is cyclobutyl or H; $R_5$ is one of the preferred or more preferred 5-membered unsaturated heterocyclic ring structures specified above; and $R_8$ is H or phenyl (optionally substituted by halo). Examples of compounds falling within this definition are:

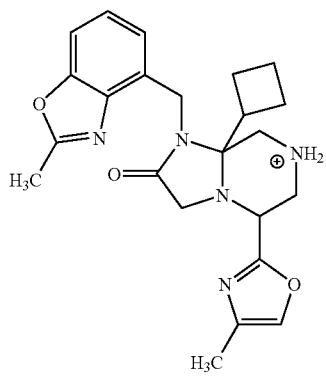

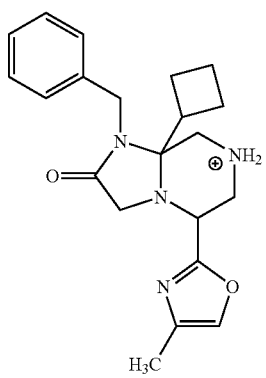

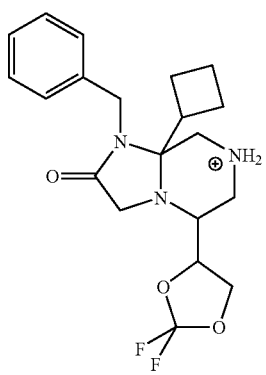

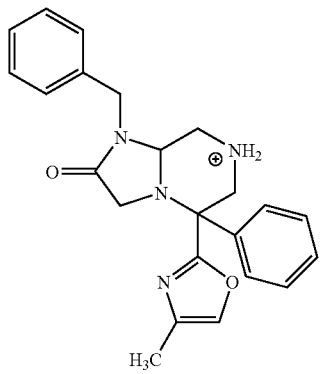

-continued

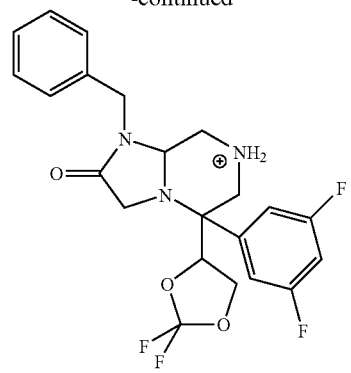

In another aspect, A is N; B is —CH$_2$—; G is oxygen; R$_1$ is hydrogen; R$_2$ is C$_{1-10}$ alkyl, for example n-C$_5$H$_{11}$, or —CH$_2$-aryl, for example —CH$_2$—C$_6$H$_5$ (optionally substituted as described below), or —CH$_2$-heterocyclic aryl, for example —CH$_2$-benzoxazole, CH$_2$-pyridyl or CH$_2$-pyrimidyl (optionally substituted as described below), a —CH$_2$-heterocyclic group (optionally substituted as described below), or a —CH$_2$— substituted C$_5$ cycloalkyl (optionally substituted as described above); R$_3$ is cyclobutyl or H; R$_5$ is —CH$_2$—O—CH$_3$; and R$_8$ is H or phenyl (optionally substituted by halo). Examples of compounds falling within this definition are:

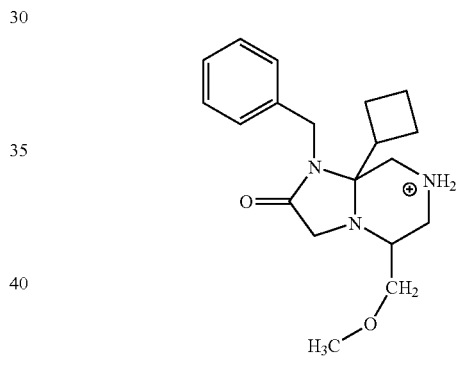

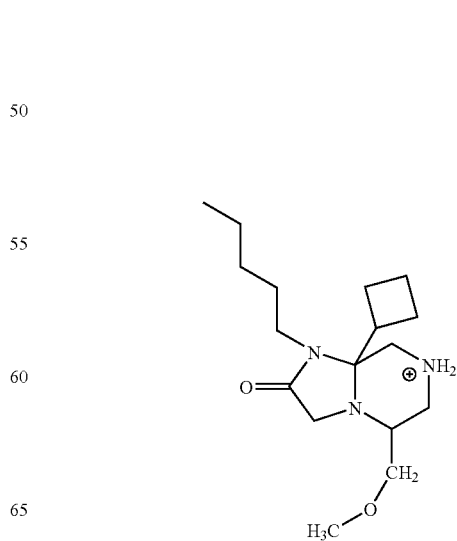

-continued

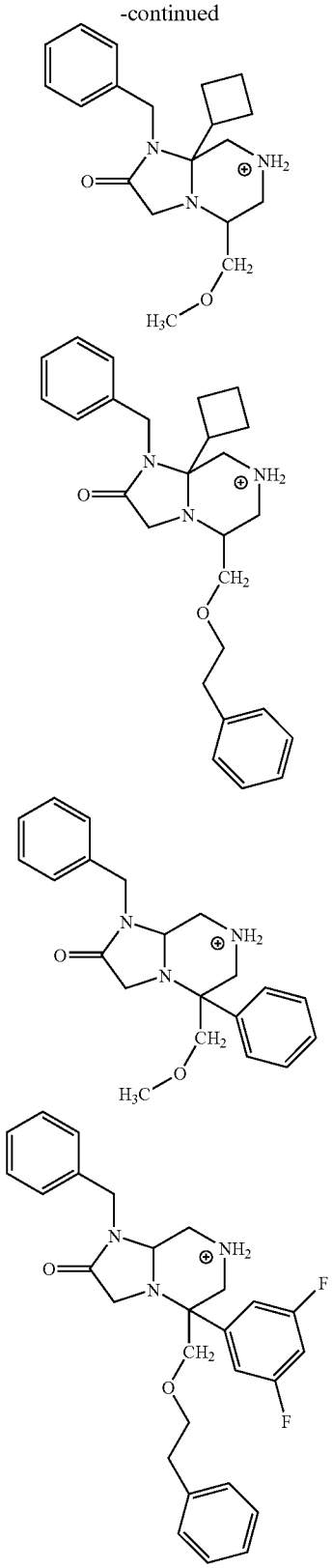

In another aspect, A is N; B is —CH$_2$—; G is oxygen; R$_1$ is hydrogen; R$_2$ is C$_{1-10}$ alkyl, for example n-C$_5$H$_{11}$, or —CH$_2$-aryl, for example —CH$_2$—C$_6$H$_5$ (optionally substituted as described below), —CH$_2$—C$_{10}$H$_7$ (optionally substituted as described below) or —CH$_2$-heterocyclic aryl for example —CH$_2$-benzoxazole, —CH$_2$-pyridyl or —CH$_2$— pyrimidyl (optionally substituted as described below) or a —CH$_2$-heterocyclic group (optionally substituted as described below); R$_3$ is hydrogen or cyclobutyl; R$_5$ is one of the preferred or more preferred 5-membered unsaturated heterocyclic ring structures specified above; and R$_8$ is phenyl, 3,5-difluorophenyl or H. Examples of compounds falling within this definition are:

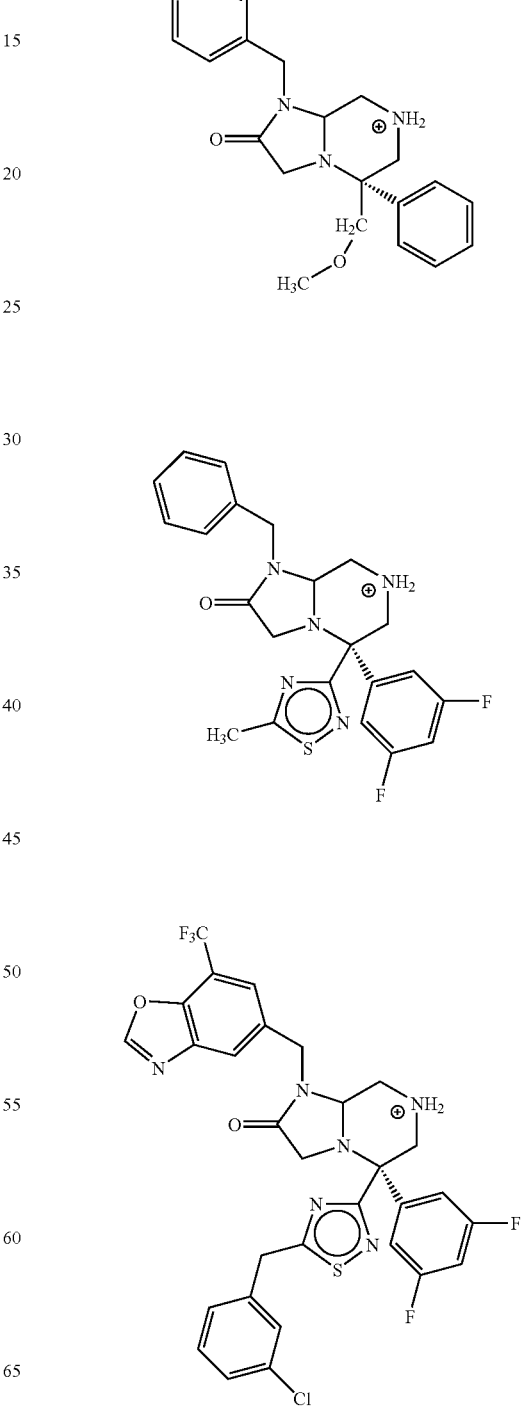

-continued

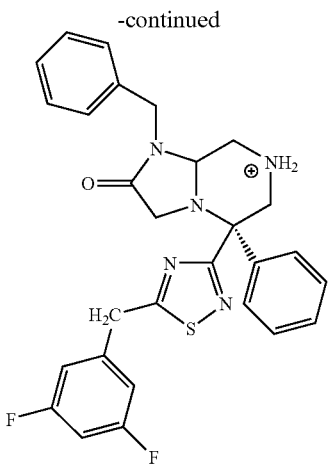

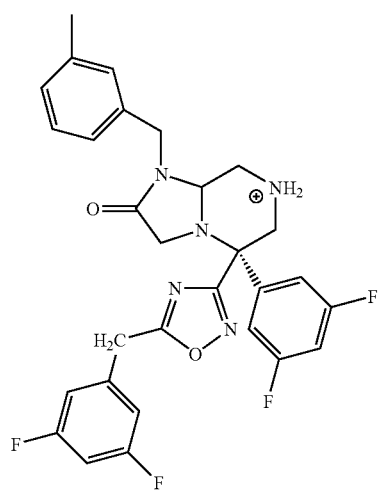

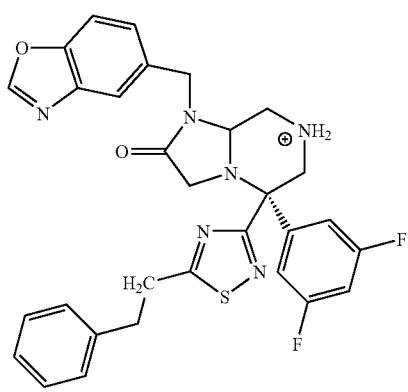

-continued

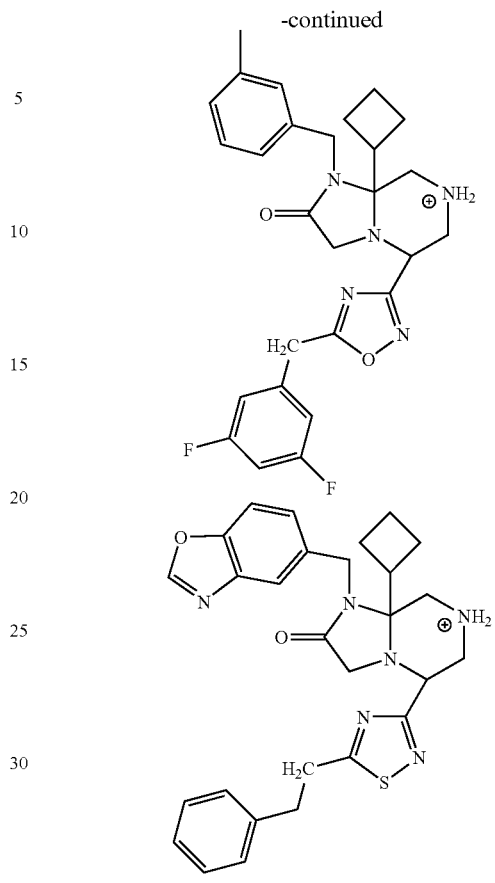

In the present context alkyl may be straight or branched. Where the alkyl is $C_{1-6}$ alkyl, this may for example be methyl, ethyl, propyl, isopropyl, butyl, tert.butyl, pentyl or hexyl. The term "lower alkyl" designates $C_{1-4}$ alkyl which may be straight or branched, such as methyl, ethyl, propyl, isopropyl, butyl or tert.butyl.

The term "alkenyl" designates a $C_2$-$C_6$ straight or $C_3$-$C_6$ branched alkyl group which contains a double bond, such as 2-propenyl, 2-butenyl, 2-pentenyl, 2-hexenyl, 2-methyl-2-propenyl or 3-methyl-2-butenyl. The term "haloalkenyl" designates an alkenyl group as defined above which may be substituted by one or more halo e.g. F, Cl, Br or I.

The term "alkynyl" designates a $C_2$-$C_6$ straight or $C_3$-$C_6$ branched alkyl group containing a triple bond, such as 2-propynyl, 2-butynyl, 2-pentynyl, 2-hexynyl or 4-methyl-2-pentynyl. The term "haloalkynyl" designates an alkynyl group as defined above which may be substituted by one or more halo e.g. F, Cl, Br or I.

The term "aralkyl" designates a lower alkyl group (as herein defined) which, in turn, may be substituted with an aryl group, preferably a phenyl, heterocyclic aryl or naphthyl group which in turn may be substituted, for example by one or more of halo, hydroxy, $C_{1-6}$ alkyl, $C_{1-6}$ haloalkyl, $C_{1-8}$ alkoxy, $C_{1-6}$ haloalkoxy, $C_{2-6}$ alkenyl, $C_{2-6}$ haloalkenyl, $C_{2-6}$ alkynyl or $C_{2-6}$ haloalkynyl. Preferred aralkyl are benzyl, 1- and 2-phenylethyl, 1-, 2- and 3-phenylpropyl, 1-methyl-1-phenylethyl, 6-ethyl benzoxazole and —CH$_2$-naphthyl. Where the aryl group, preferably phenyl, heterocyclic aryl or naphthyl group, of the aralkyl is substituted with haloalkyl (preferably $C_{1-4}$ alkyl), halogen, lower alkyl, or $C_{1-6}$ alkoxy, they may be mono-, di- or tri-substituted and when they are di- or tri-substituted the substituents may be the same or different. Preferred substituents on the phenyl are —$CF_3$, chloro, bromo, $C_{2-6}$ alkyl and $C_{4-8}$ alkoxy. Preferred substituents on the naphthyl are —$CF_3$, chloro, bromo, $C_{1-4}$ alkyl (such as methyl), and $C_{3-7}$ alkoxy.

The term "heterocycle" designates a heterocyclic group, which may be a heterocyclic aryl group as described above or non-aromatic heterocyclic group each of which may be substituted by one or more of halo, hydroxy, $C_{1-6}$ alkyl, $C_{1-6}$ haloalkyl, $C_{1-8}$ alkoxy, $C_{1-6}$ haloalkoxy, $C_{2-6}$ alkenyl, $C_{2-6}$ haloalkenyl, $C_{2-6}$ alkynyl or $C_{2-6}$ haloalkynyl. The preferred heterocycles of the invention are 5 membered rings optionally substituted as described above.

The term "halogen" designates F, Cl, Br, or I; Cl, Br and F are preferred.

The term "alkoxy" denotes a $C_1$-$C_6$ straight or $C_3$-$C_6$ branched alkoxy group. Examples of such groups are methoxy, ethoxy, propoxy, butoxy, pentoxy, hexoxy, 2-methyl ethoxy, 2-ethyl propoxy and 1-ethyl-2-methyl-propoxy.

The term "haloalkoxy" designates an alkoxy group as defined above which may be substituted by one or more halo e.g. F, Cl, Br or I.

Examples of suitable salts include inorganic and organic acid addition salts such as hydrochloride, hydrobromide, sulphate, phosphate, acetate, fumarate, maleate, citrate, lactate, tartrate, oxalate or similar pharmaceutically-acceptable inorganic and organic acid addition salts.

The compounds of the invention exist in geometrical and/or optical isomers. The present invention encompasses all enantiomers and mixtures thereof. Preferred is the isomer shown below:

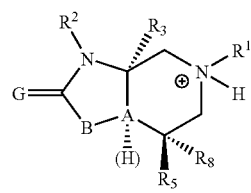

The compounds of the invention are selective $m_1$-muscarinic receptor agonists and therefore useful in methods for the treatment of disorders, such as Alzheimer's disease, caused by malfunction of the acetylcholine (AcCh) or muscarinic system, by administering a non-toxic effective amount thereof to a mammalian, normally human, subject.

Compounds of the invention may be made by methods known in the art.

Thus, for example, compounds in which A is N, B is —$CH_2$— and $R_5$ is —$CH_2$—O—Me may be made in accordance with the following synthetic pathway:

Reaction Scheme 1

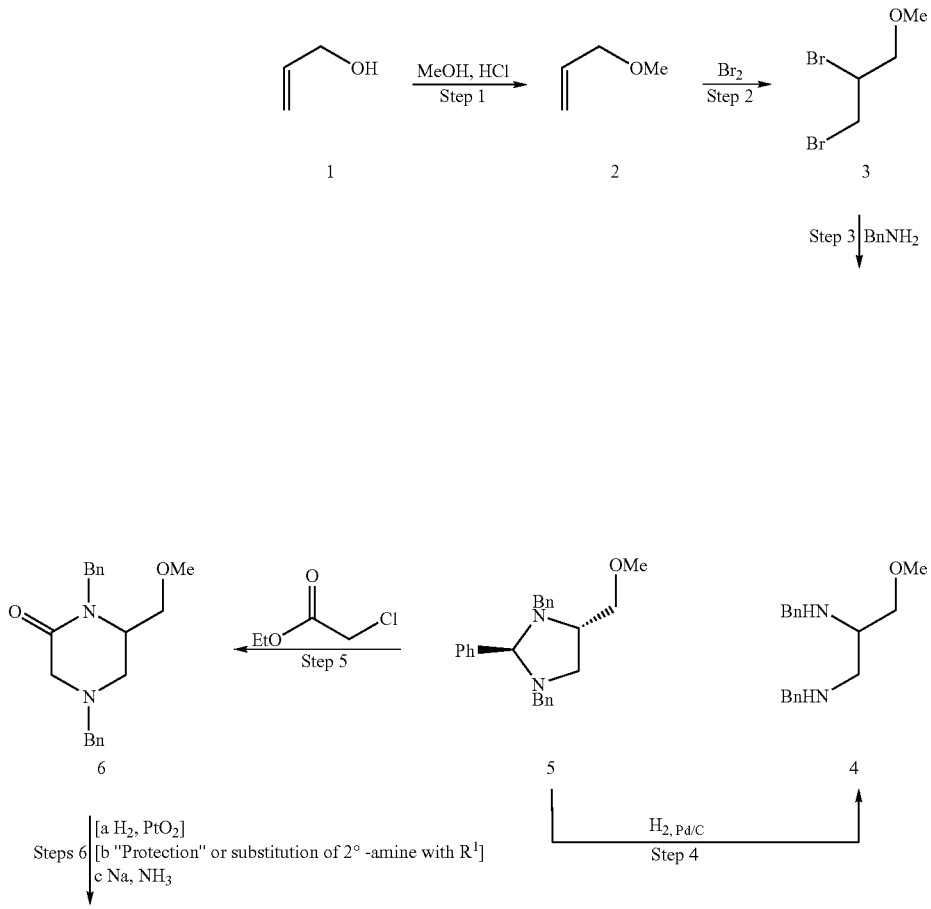

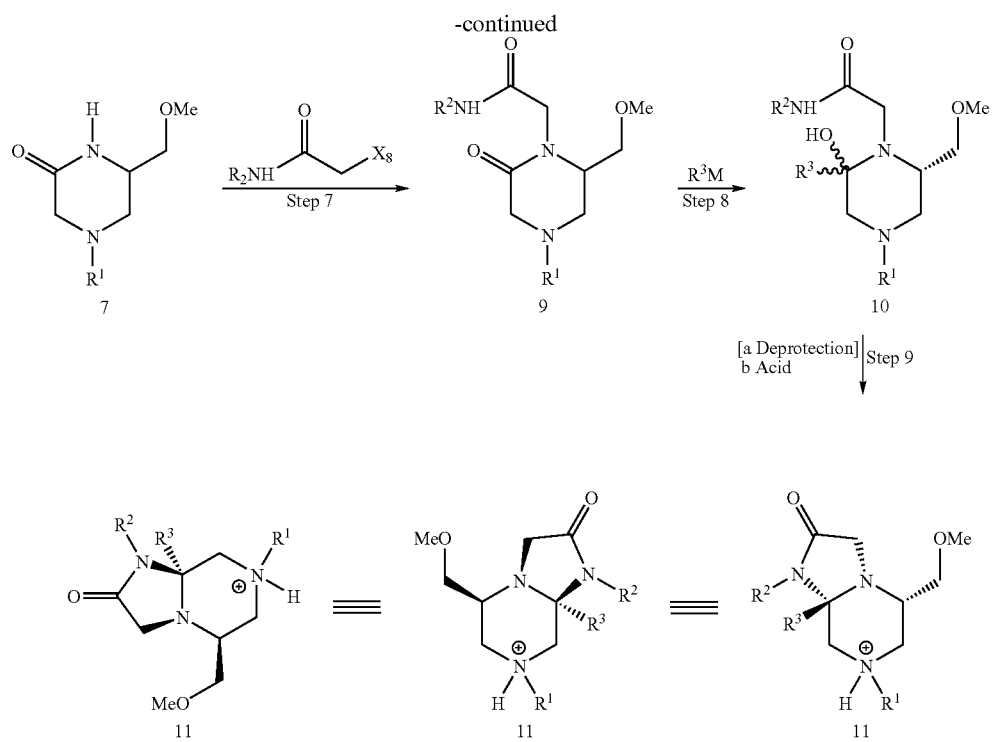

Steps 1 & 2

Treatment of allyl alcohol 1 with hydrochloric acid in methanol gives the known ether 2, which is converted to the known dibromide 3, by addition of bromine.

Steps 3 & 4

Nucleophilic displacement by excess benzylamine in the presence of a high boiling solvent, under an inert atmosphere yields the diamine 4. In the presence of air the geminal diamine 5 is formed. This may be reconverted to the diamine 4 by hydrogenolysis. In a similar manner, reaction with p-methoxybenzylamine gives analogous products which may be used in subsequent reactions in an identical way. The p-methoxybenzylamine derivatives have the advantage that they are cleaved more easily than the benzylamine derivatives (cf. step 6).

Step 5

Reaction with ethyl chloroacetate or a range of other α-haloesters (eg α-bromo- or α-iodoesters bearing other alkyl substituents) yields the piperidinone 6, plus the regioisomer together with diacylated and dialkylated products. Reaction at −10° C., in methylene chloride, with 1.2 equivalents of α-chloroacetyl chloride gives a mixture from which the desired isomer 6 can be isolated in 70% yield. The piperidinone 6, serves as a common starting material for all subsequent reactions. Reactions shown in brackets (Steps 6 & 9) are used as appropriate according to the substituents/protecting groups present. The following examples illustrate the general methodology.

Steps 6-9 (a) Compounds 7-11 where $R_1$=Bn or p-MeOBn; $R_2$=any alkyl, aryl or benzyl, $R_3$=any alkyl, aryl or benzyl Cleavage of the amidic benzylamine substituent with sodium in liquid ammonia gives the amide 7 ($R_1$=H), which is treated sequentially with sodium hydride in DMSO (or other strong bases) and the haloamide 8 (X=preferably Cl, but also Br or I) to give the tertiary amide 9. Reaction with an organometallic reagent such as a Grignard or organolithium reagent gives the aminol 10, which spontaneously cyclises and upon acidification yields the salt 11.

(b) Compounds 7-11 where $R_1$ is H; $R_2$ is any alkyl, aryl or benzyl, $R_3$ is H or any alkyl, aryl or benzyl Hydrogenolysis of the benzylic amine yields a secondary amine, which is protected as the silyl ether with tri-isopropylsilyl-, t-butyldimethylsilyl- or t-butyldiphenylsilyl-trifluoromethanesulfonate. Cleavage of the amidic benzylic substituent with sodium in liquid ammonia yields the secondary amide 7 ($R_1$=$^i$Pr$_3$Si, $^t$BuMe$_2$Si or $^t$BuPh$_2$Si). Subsequent reactions, follow the sequence outlined above under (a), except that deprotection with a nucleophilic fluoride source is required in Step 9. This is typically tetrabutylammonium fluoride, cesium fluoride or another comparable reagent known in the prior art.

(c) Compounds 7-11 where $R_1$ is any alkyl, aryl or benzyl; $R_2$ is any alkyl, aryl or benzyl, $R_3$ is H or any alkyl, aryl or benzyl This pathway follows the sequence under (b) above, except that in step 6b, the secondary amine is converted to a tertiary amine by reaction with an alkylating reagent (eg. haloalkane or benzylic halide) or an arylating reagent (eg ArBr, Cu or ArCl, PdCl$_2$(PAr$_3$)$_2$ with the aminostannane). No deprotection is required in step 9.

Compounds in which A is CH, B is O and $R_5$ is 4-methyloxazol-2-yl or —CH$_2$—O—Me may be made in accordance with the following alternative synthetic pathways:

Reaction Scheme 2

M₁-Muscarinic Receptor Agonist Synthetic Route:

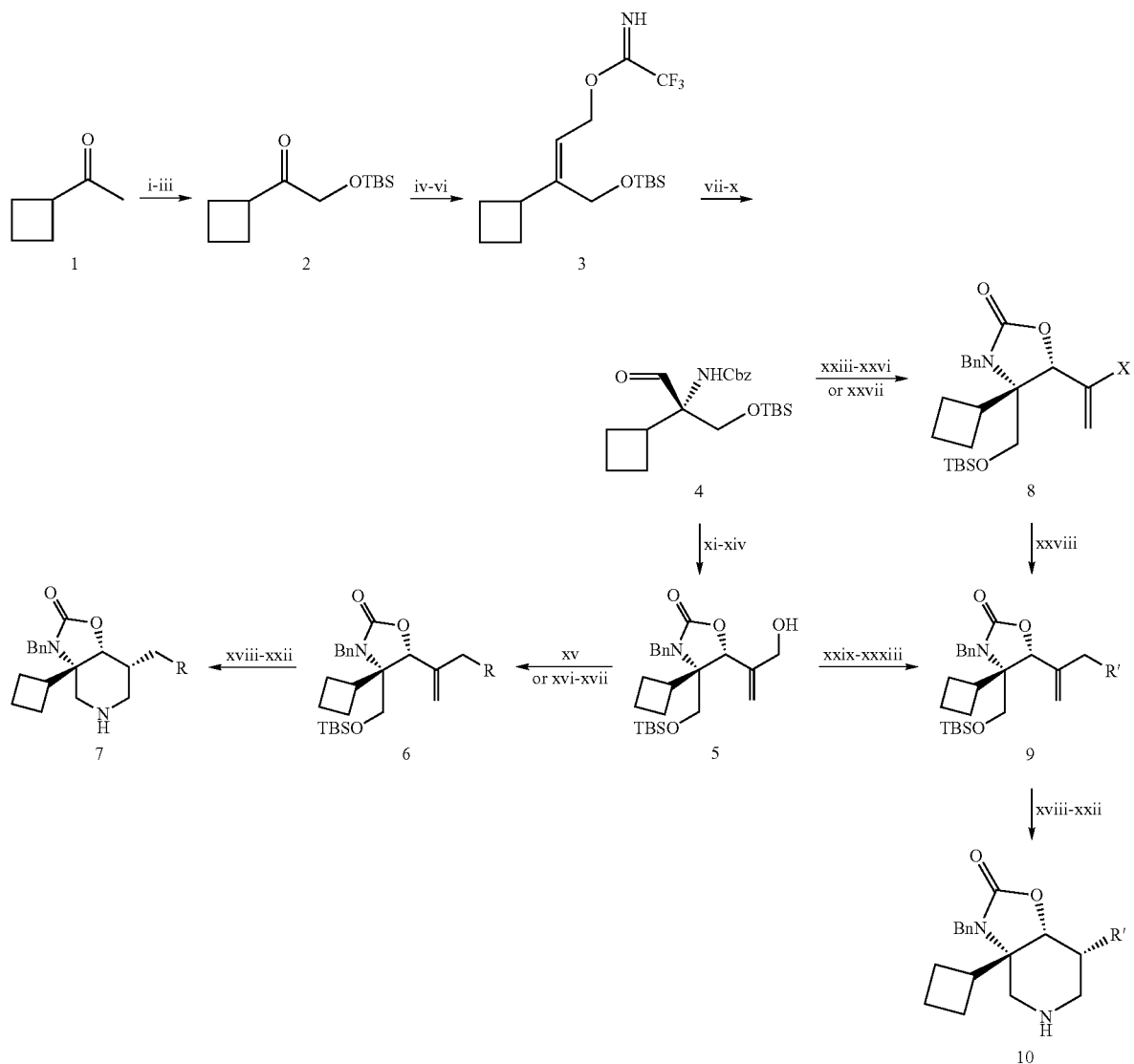

Scheme 1. Reagents: i. Br₂, MeOH; ii. KCO₂H, MeOH; iii. TBSCl, Imidazole, DCM; iv. (EtO)₂PCH₂CO₂Et, NaH, THF; v. DIBAL-H, THF; vi. CF₃CN, NaH, THF; vii. xylene; viii. NaBH₄, EtOH; ix. CbzCl, Et₃N, DCM; x. O₃, PPh₃, DCM; xi. CH₂=CMeMgBr, THF; xii. mCPBA, DCM; xiii. TMP, n-BuLi, THF; xiv. BnBr, NaH, THF; xv. RI, NaH, THF; xvi. CBr₄, PPh₃, MeCN; xvii. RLi or RNa, THF; xviii. a. BH₃, THF; b. EtOH, NaOAc, H₂O₂; xix. TBAF, THF; xx. MsCl, Et₃N, DCM; xxi. BnNH₂; xxii. Pd/C, HCO₂H, MeOH; xxiii. CH₂=CMeMgBr, THF; xxiv. BnBr, NaH, THF; xxv. O₃, PPh₃, DCM; xxvi. KHMDS, PhN(Tf)₂, THF; xxvii. HC≡CXLi or HC≡CXMgBr, THF; xxviii. R'X, Pd(0), THF; xxix. Dess Martin periodinane, DCM; xxx. 2-methyl-2-butene, NaClO₂, NaH₂PO₄, t-BuOH/water; xxxi. i-BuO-COCl, NMM, 2-aminopropanol, THF; xxxii. Dess Martin periodinane, DCM; xxxiii. 2,6-di-t-Butyl-4-methylpyridine, PPh₃, Cl₂BrCCCl₂Br, DBU, DCM, CH₃CN.

M1—Muscarinic Receptor Agonist Synthesis

The protected α-amino-aldehyde 4 was identified as a key intermediate in the synthesis of the target molecules 7 and 10 since stereoselective vinyl Grignard addition followed by functional group modification and cyclisation would lead to the required piperidines. The introduction of the tertiary amino group into the aldehyde 4 was as a key step in the synthesis which was to be accomplished by rearrangement of an allylic trifluoroacetimidate.

The protected hydroxyketone 2 was prepared from the commercially available cyclobutyl methyl ketone 1 by bromination, hydrolysis of the bromoketone so obtained and protection. Condensation of the ketone 2 with triethyl phosphonoacetate followed by reduction using diisobutyla-luminium hydride gave the corresponding allylic alcohol which was converted into the trifluoroacetimidate 3 using trifluoroacetonitrile. On reflux in xylene this trifluoroacetimidate rearranged to the isomeric tertiary trifluoroacetamide which was taken through to the aldehyde 4 by removal of the trifluoroacetyl group using sodium borohydride, N-protection and ozonolysis.

Addition of prop-2-enyl magnesium bromide was stereoselective and on work-up was accompanied by cyclisation to give a carbamate which was converted into the intermediate 5 by epoxidation, lithium 2,2,6,6-tetramethylpiperidide induced epoxide-allylic alcohol rearrangement and N-protection using sodium hydride benzyl bromide.

The next steps involved modification of the hydroxyl groups to give access to various side-chains. Thus, for example, O-methylation using methyl iodide and sodium hydride gave the methyl ether 6 (R=OMe) which was taken through to the target 7 (R=OMe) by hydroboration with an oxidative work-up, removal of the silyl protecting group, mesylation of both hydroxyl groups, and displacement of the mesylates followed by hydrogenolysis of the N-benzyl group.

In an approach to the analogue with a 4-methyloxazol-2-yl side chain 10 (R'=4-methyloxazol-2-yl), the alcohol 5 was oxidised to the corresponding acid over two steps, and the acid converted into its amide using 2-aminopropanol. Cyclisation was achieved by oxidation to the aldehyde using the Dess Martin periodinane followed by dehydration to give 9 (R'=4-methyloxaxol-2-yl). However, in this case, conversion to the target 10 (R'=4-methyloxazol-2-yl) was inefficient because of competing elimination of the carbamate after the hydroboration step. Ozonolysis of the alkene 8 (X=Me) gave the corresponding ketone which was converted into its enol triflate 8 (X=OTf) for palladium cataylsed coupling with aryl halides.

Compounds in which A is CH, B is N and $R_5$ is —$CH_2$—O—Me may be made in accordance with the following synthetic pathway:

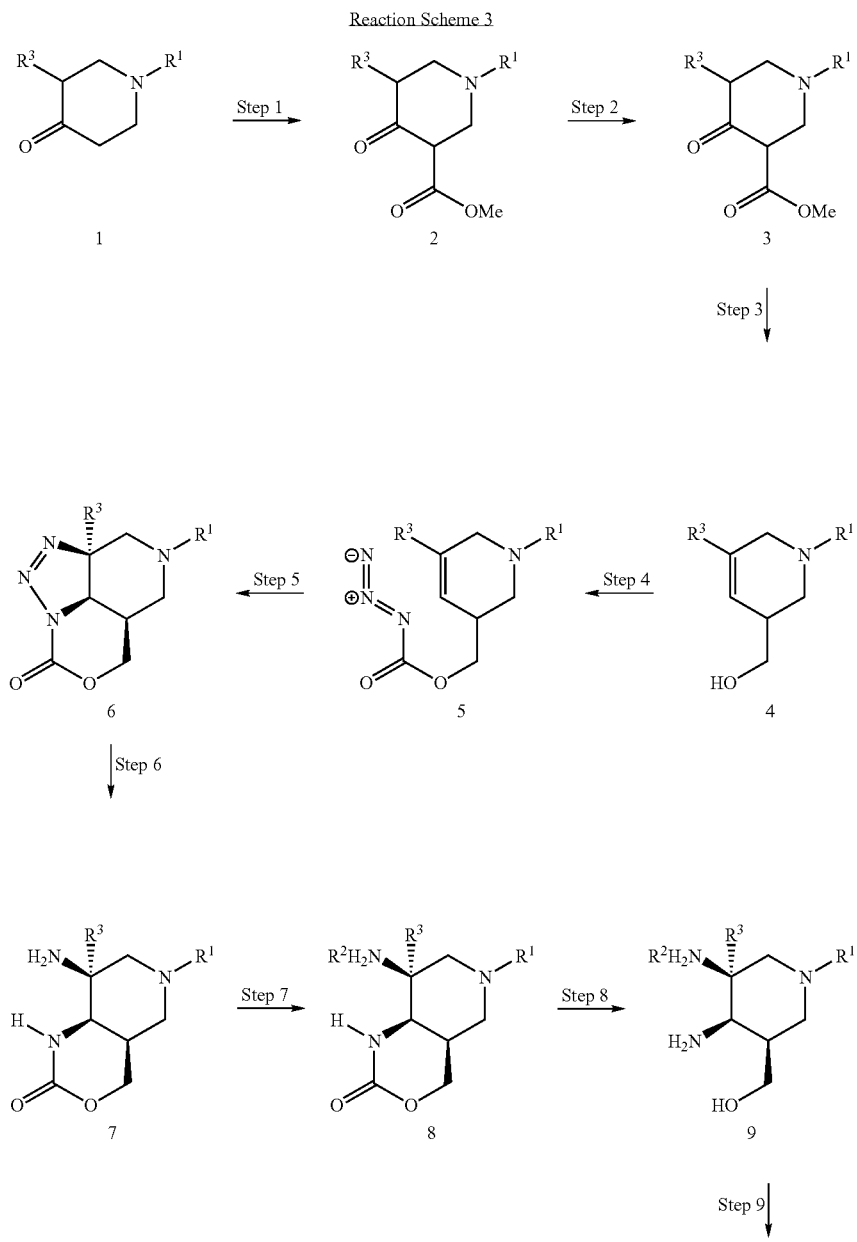

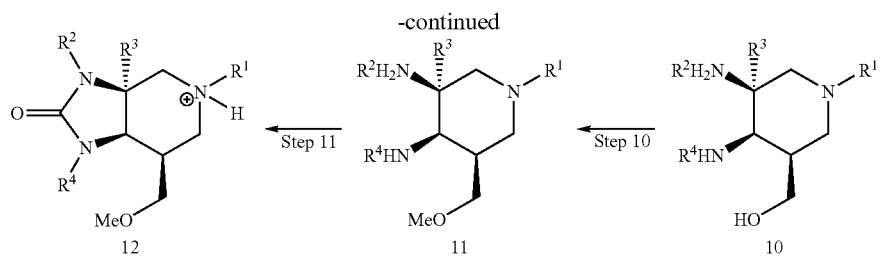

Step 1

The alkylation of the piperidinone 1 ($R_1$=Bn; $R_3$=H) using sodium hydride and dimethylcarbonate has been reported (S. Singh, G. P. Basnadjian, K. S. Avor, B. Pouw, T. W. Seale, Synthesis and ligand binding studies of 4'-iodobenzoyl esters of tropanes and piperidines at the dopamine transporter, J. Med. Chem., 1997, 40, 2474-2481). Moreover the compound 2 ($R_1$=Bn; $R_3$=H) has been reported to be commercially available (H.-J. Altenbach and G. Blanda, A novel building block for the synthesis of isofagomin analogues, Tetrahedron: Asymmetry, 1998, 9, 1519-1524) and has been converted into the compound 4 ($R_1$=Bn, $R_3$=H). Adaption of the known routes to these compounds enables the synthesis of compounds 1 and 2 in which $R_1$=alkyl, benzyl and $CH_2$-heteroaromatic.

Step 2

Generation of the dianion of the β-ketoester 2, with LDA (lithium di-isopropylamide) or a comparable strong base and treatment with an electrophilic alkylating reagent ($R_3X$, X=Cl, Br, I, OTs, OMs or a comparable nucleofuge), enables the synthesis of compounds 3 ($R_3$=n-alkyl, benzyl, $CH_2$-heteroaromatic, or allyl or derivatives thereof). In the cases in which $R_3$ cannot act as a suitable alkylating agent (eg. cyclopropyl, cyclobutyl, cyclopentyl, cyclohexyl, isopropyl and other secondary and tertiary substituents), the desired compounds are prepared by an alternative route. Thus a ketone ($CH_3COCH_2R_3$) is treated with formaldehyde (or a synthetic equivalent) and ammonia or an appropriate amine (eg. $R_1NH_2$) to give the piperidinone 1 directly.

Step 3

Formation of the p-toluenesulfonylhydrazone with p-toluenesulfonylhydrazine and treatment with three equivalents of base, followed by lithium aluminium hydride reduction gives the desired compound 4 ($R_3$=H; Shapiro reaction, cf. Altenbach & Blanda, as above).

However when $R_3$ is not hydrogen, it is more advantageous to reduce the ketone with sodium borohydride and to effect β-elimination with p-toluenesulfonyl chloride to give the α,β-unsaturated ester. Treatment with LDA generates the enolate which is reprotonated at the a-position with t-butyl bromide (or a comparable proton source) to give the β,γ-unsaturated ester, which in turn is reduced with lithium aluminium hydride to give the homoallylic alcohol 4.

Steps 4 & 5

The homoallylic alcohol 4 is treated with potassium t-butoxide and butyl lithium at low temperatures in non-polar solvents to generate the potassium alkoxide. This is reacted in turn with a toluene solution of phosgene and an alkali or alkaline metal azide salt to yield the acyl azide 5. Alternatively the potassium alkoxide of the homoallylic alcohol 4 is treated with azidocarbonic acid methyl ester. Warming to room temperature or slightly higher effects cyclisation to yield the triazoline 6.

Step 6

Reductive cleavage of the triazoline 6 to the aminourethane 7 may be achieved using a variety of conditions. Hydrogenolysis with hydrogen catalysed by palladium or platinum is cheapest and most effective, however if $R_1$=Bn and it is desirable for this group to be retained, triphenylphosphine or a comparable trivalent phosphorus reagent plus water or ammonium hydroxide or sodium hydroxide is preferable. Reduction with lithium aluminium hydride yields 10 ($R_1$ & $R_3$ as 6; $R_2$=H; $R_4$=$CH_3$).

Step 7

The aminourethane 7 may be alkylated on the primary amino group with an electrophilic reagent $R_2X$, within the usual scope of such reactions ($R_2$=n-alkyl, benzyl, $CH_2$-heteroaromatic, or allyl or derivatives thereof; X=Cl, Br, I, OTs, OMs or a comparable nucleofuge).

Steps 8 and 9

Cleavage of the urethane group with refluxing concentrated sodium hydroxide or concentrated hydrochloric acid containing a trace of p-toluenesulfonic acid yields the primary amine 9, which may be alkylated ($R_4$) as in step 7. In this case the regioselectivity is poorer and some multiple alkylation products are also formed.

Step 10

Treatment with potassium t-butoxide and no more than one equivalent of dimethylsulfate yields the methyl ether 11.

Step 11

Treatment with phosgene, diphosgene or triphosgene or any of a number of synthetic equivalents, plus a base yields the urea, which is converted to the salt 12, by treatment with an acid. If desired, the benzyl group ($R_1$) may be removed by hydrogenolysis using hydrogen and platinum or palladium catalysts and the secondary amine so formed alkylated with an electrophilic reagent R4X, within the usual scope of such reactions ($R_1$=n-alkyl, benzyl, $CH_2$-heteroaromatic, or allyl or derivatives thereof; X=Cl, Br, I, OTs, OMs or a comparable nucleofuge).

Compounds in which A is CH, B is N and $R_5$ is a 5-membered heterocyclic ring may be made following the pathway above for compounds in which A is CH, B is N and $R_5$ is —$CH_2$—O—$R_7$ starting with compound 10 and applying step 11 gives compounds 12 in which the lower most substituent is a hydroxyl group instead of a methyl ether. The hydroxyl group may be oxidised to a carboxylic acid and converted to an ester as before. The practicality of step 11 in this specific context depends on the substituents $R_1$, $R_2$ and $R_4$ on the amine groups. Compound 10 may be temporarily protected by reaction of the alkoxide (as in the original route, step 10), but with benzyl bromide to give a benzyl ether (11 Me=Bn). Step 11 follows as before to give (Me=Bn). The benzyl group is then removed using hydrogen and platinum on charcoal to give 12 (Me=H), which can be oxidised as above. In this alternative pathway, the designation 12 refers to the free amine rather than the ammonium salt shown in the scheme and the procedure is not applicable to the case where $R_1$, $R_2$ or $R_4$=Bn.

Similarly, compounds in which A is CH, B is O, G is O, $R_2$ is benzyl, $R_3$ is H, $R_5$ is —$CH_2$—O—$CH_3$ or oxazole and $R_8$ is phenyl may be made by the following reaction scheme:

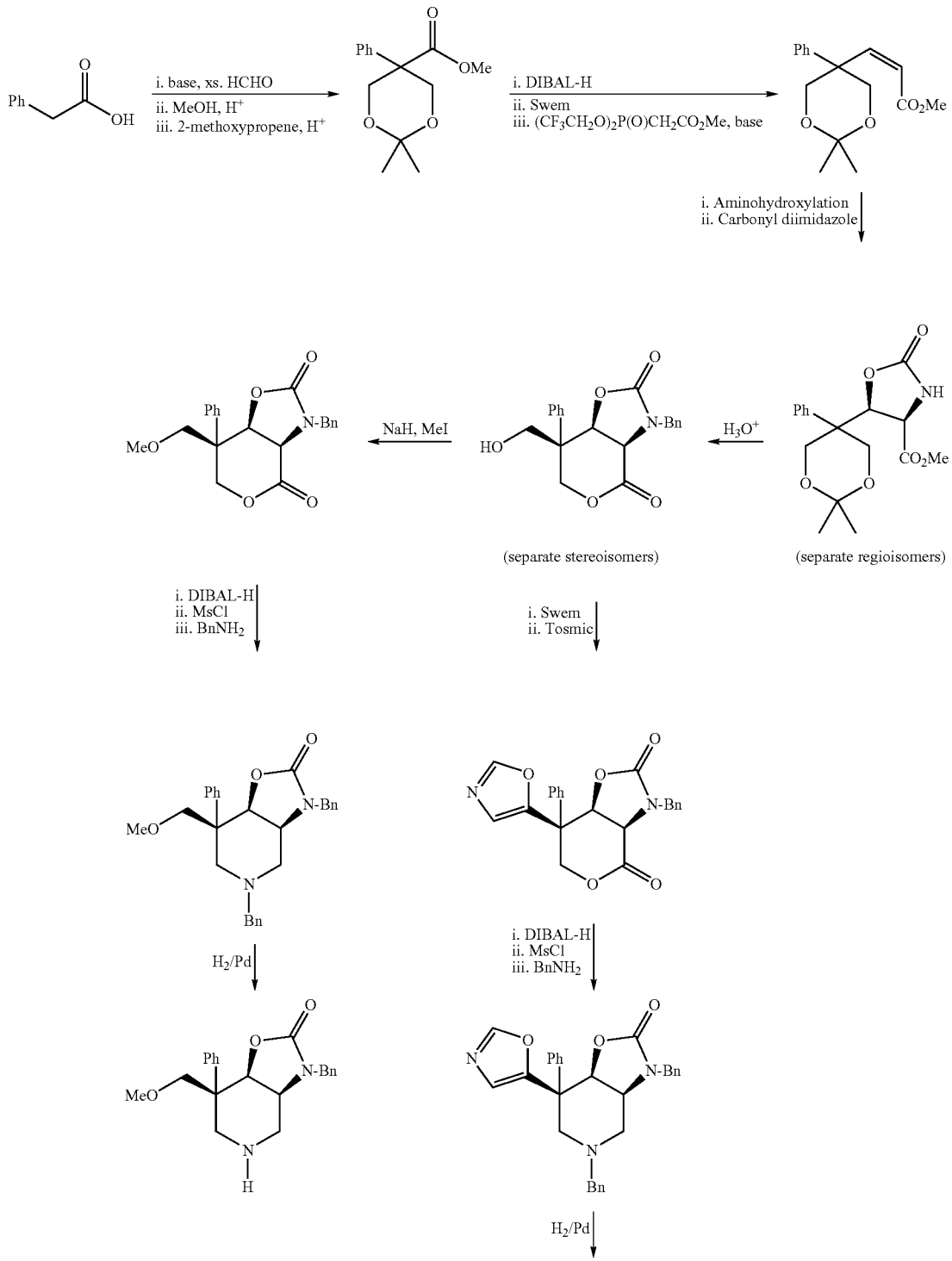

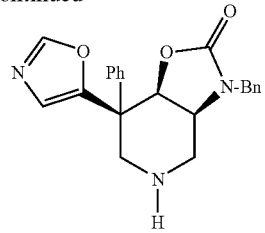

It will be appreciated that the above reaction scheme may be generalised or varied as appropriate in order to produce additional compounds in accordance with the first embodiment of the invention. This variation would be within the ability of one skilled in the art.

$M_1$ receptor activity of a compound of the invention may be examined with the rabbit vas deferens using a method developed from that described previously (Dorje F, Rettenmayr N, Mutschler E and Lambrecht G, Eur J Pharmacol 1991, 203, 417-420). The tissue is stimulated electrically to contract and the conditions are optimized so that $M_1$ receptor agonists produce a concentration-related inhibition of contraction height. Any activity at $M_2$ receptors is indicated by an increase in the contraction height. $M_2$ receptor activity may also be recorded from increases in contraction of the guinea-pig paced left atria. $M_3$ receptor activity is measured from the contraction of the guinea-pig ileum. Other methods for analysing $M_1$ receptor activity may be employed, such as those described in EP-A-0336555 and EP-A-0384288 (the disclosures of which are hereby incorporated by reference to the extent possible under the relevant national law).

In accordance with the second embodiment, the compounds of the present invention, together with a conventional adjuvant, carrier, or diluent, and if desired in the form of a pharmaceutically-acceptable acid addition salt thereof, may be placed in the form of pharmaceutical compositions and unit dosages thereof, and in such form may be employed as solids, such as tablets or filled capsules, or liquids, such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective muscarinic cholinergic agonistic amount of the active ingredient commensurate with the intended daily dosage range to be employed. Tablets containing ten (10) milligrams of the active ingredient or, more broadly, one (1) to hundred (100) milligrams, per tablet, are accordingly suitable representative unit dosage forms. The compounds of this invention can thus be used for the formulation of pharmaceutical preparations, e.g. for oral and parenteral administration to mammals including humans, in accordance with conventional methods of galenic pharmacy.

Conventional excipients are such pharmaceutically acceptable organic or inorganic carrier substances suitable for parenteral or enteral application which do not deleteriously react with the active compounds.

Examples of such carriers are water, salt solutions, alcohols, polyethylene glycols, polyhydroxyethoxylated castor oil, gelatine, lactose, amylase, magnesium stearate, talc, silicic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxiliary agents, emulsifiers, salt for influencing osmotic pressure, buffers and/or colouring substances and the like, which do not deleteriously react with the active compounds.

For parenteral application, particularly suitable are injectable solutions or suspensions, preferably aqueous solutions with the active compound dissolved in polyhydroxylated castor oil.

Ampoules are convenient unit dosage forms.

Tablets, dragees or capsules having talc and/or a carbohydrate carrier or binder or the like, the carrier preferably being lactose and/or corn starch and/or potato starch, are particularly suitable for oral application. A syrup, elixir or the like can be used in cases where a sweetened vehicle can be employed.

Generally, the compounds of this invention are dispensed in unit form comprising 1-100 mg in a pharmaceutically acceptable carrier per unit dosage.

The dosage of the compounds according to this invention is 1-100 mg/day, preferably 10-70 mg/day, when administered to patients, e.g. humans, as a drug.

A typical tablet which may be prepared by conventional tabletting techniques contains:

| | |
|---|---|
| Active compound | 5.0 mg |
| Lactosum | 67.8 mg Ph.Eur. |
| Avicel ® | 31.5 mg |
| Amberlite ® | 1.0 |
| Magnesli stearas | 0.25 mg Ph.Eur. |

In accordance with the third, fourth and fifth embodiments, the compounds of the invention are useful in the treatment and manufacture of medicaments for the treatment of symptoms related to a reduction of the cognitive functions of the brain of mammals, when administered in an amount effective for stimulating the cognitive functions of the forebrain and hippocampus. The important stimulating activity of the compounds of the invention includes both activity against the pathophysiological disease, Alzheimer's disease, as well as against normal degeneration of brain function.

The compounds of the invention may accordingly be administered to a subject, e.g. a living animal body, including a human, in need to stimulation of the cognitive functions of the forebrain and hippocampus, and if desired in the form of a pharmaceutically-acceptable acid addition salt thereof (such as hydrobromide, hydrochloride, or sulfate, in any event prepared in the usual or conventional manner, e.g. evaporation to dryness of the free base in solution together with the acid) ordinarily concurrently, simultaneously, or together with a pharmaceutically-acceptable carrier or diluent, especially and preferably in the form of a pharmaceutical composition thereof, whereof by oral, rectal, or parenteral (including subcutaneous) route, in an effective forebrain and hippocampus stimulating amount, and in any event an amount which is effective for improving the cognitive function of mammals due to their muscarinic cholinergic receptor agonistic activity.

Suitable dosage ranges are 1-100 milligrams daily, 10-100 milligrams daily, and especially 30-70 milligrams daily, depending as usual upon the exact mode of administration, form in which administered, the indication toward which the administration is directed, the subject involved and the body weight of the subject involved, and the preference and experience of the physician or veterinarian in charge.

EXAMPLES

The invention is further illustrated by the following non-limiting example.

Example 1

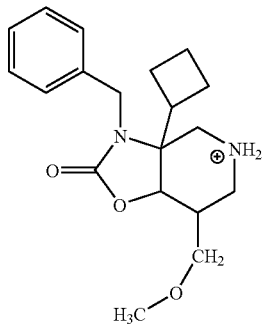

3-Benzyl-3a-cyclobutyl-7-methoxymethyl-2-oxo-octahydro-oxazolo[4,5-c]pyridin-5-ium The above compound was synthesised by the method of reaction scheme 2 above. The compound was characterised by IR spectroscopy.

Pharmacology

Functional Assays of M1 Receptor Activity

Initial evaluation of the test compound is by assay of functional tissue responses. This has the advantage that it readily discriminates between agonist, partial agonist and antagonist activity.

M1—Vas Deferens Preparations

Male New Zealand white rabbits (1.47-3.4 Kg) are killed by a blow to the back of the head and vasa deferentia removed, dissected free of connective tissue and divided into prostatic and epididmyal portions. Each segment is mounted on a tissue holder and passed through two ring electrodes (5 mm apart). They are immersed in a modified low $Ca^{2+}$ Krebs solution at 32+/−0.5° C. and gassed with 5% $CO_2$ in oxygen. Yohimibine (1.0 mM) is present throughout to block prejunctional a2-adrenoceptors. The upper end of the tissue is attached by cotton thread to an isometric transducer (MLT020, ADInstruments). Tissues are left to equilibrate for at least 45 min at passive force of 0.75-1 g. Field stimulation is then applied by repeated application of single pulses (30V, 0.05 Hz, 0.5 ms). Isometric tension is recorded by computer at a sampling rate of 100 Hz, using Powerlab/200 (ADInstruments) software and MacLab bridge amplifiers.

M2—Guinea-Pig Atria

Guinea-pigs are killed by a blow to the back of the head and left atrium removed. The atrium is secured to a pari of stainless steel electrodes by means of a cotton thread and immersed in the organ bath containing gassed Krebs solution with normal $Ca^{2+}$ at 32+/−0.5° C. Atria are paced at 2 Hz with square-wave pulses of 0.5 ms pulse width. Isometric contractions are recorded by computer or polygraph.

M3—Guinea-Pig Ileum

Sections (2 cm) are cut from the ilium of the killed guinea-pigs, 10 cm from the ileo-caecal junction. One end is attached to a tissue holder/aerator and the other end via a cotton thread to an isometric transducer. The tissue is immersed in gassed normal $Ca^{2+}$ Krebs solution at 32+/−0.5° C. A resting tension of 0.5 g is applied and isometric contractions measured by computer or polygraph.

Agonist Concentration-Response Curves

Following at least 30 min equilibration to allow twitches or tension to stabilize, cumulative concentration-response curves for the muscarinic agonists are constructed. The concentration is increased in half logarithmic increments after the contraction in the presence of each concentration has plateaued. Steady-state contractions at each concentration are measured and the inhibition expressed as a percentage of the baseline twitch height in atria and vas deferens or as the maxi contraction in the ileum. EC50 values for the muscarinic agonists are determined from individual curves as the molar concentration required for 50% inhibition of twitch height or the 50 maximum contraction (ileum). Geometric mean EC50 values and their 95% confidence limits are calculated.

It was found that the compound of Example 1 was a 50% partial M1 agonist with a potency (EC50 value) of $10^{-7}$M.

The invention claimed is:

1. A compound of the formula:

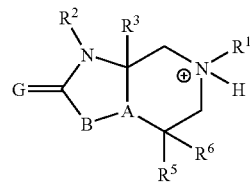

or a pharmaceutically acceptable salt thereof, wherein:

A is CH or nitrogen;

B is —$CH_2$—, —CHF—, —$CF_2$—, $NR_4$ or O, with the proviso that when A is N, B is —$CH_2$—, —CHF— or —$CF_2$—;

G is oxygen, $R_1$ is hydrogen or $C_{1-6}$ alkyl;

$R_2$ is $C_{1-8}$ alkyl, —$CH_2$-aryl, —$CH_2$-heterocycle, —$CH_2$-substituted $C_5$ cycloalkyl or a —$CH_2$-substituted heterocycle, each of which may be optionally substituted with one or more of halo, hydroxyl, $C_{1-6}$ alkyl, $C_{1-6}$ haloalky, $C_{1-8}$ alkoxy, $C_{1-6}$ haloalkoxy, $C_{2-6}$ alkenyl, $C_{2-6}$ haloalkenyl, $C_{2-6}$ alkynyl or $C_{2-6}$ haloalkynyl;

$R_3$ is hydrogen; cyclobutyl, cyclopropyl, methyl, ethyl, isopropyl, butyl, secbutyl;

R5 is a 5-membered unsaturated heterocyclic ring having one of the following structures:

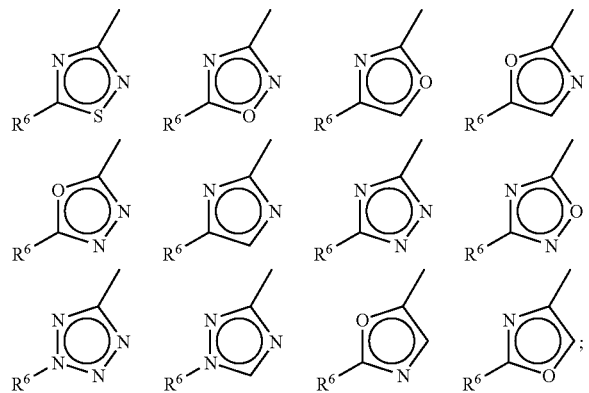

R6 is methyl, aralkyl, arylamino, aralkyl substituted by one or more halo and having a methylene group linking the aryl to the unsaturated 5-membered ring, aralkyl substituted by one or more halo and having an ethylene group linking the aryl to the unsaturated 5-membered ring; or R5 may also be C2-C4-aralkyl, —CH2—O—R7 where R7 is C1-6 alkyl, C2-6 alkenyl, C2-6 alkynyl, C2-C4 aralkyl which groups may be optionally substituted with fluoro or hydroxy; and R8 is hydrogen phenyl or halo-substituted phenyl;

with the proviso that when either R3 or R8 is not hydrogen, the other is hydrogen.

2. A compound according to claim 1, wherein

R1 is H;

R2 is —CH2-aryl optionally substituted with one or more of halo, hydroxy, C1-6 alkyl, C1-6 haloalkyl, C1-8 alkoxy, C1-6 haloalkoxy, C2-6 alkenyl, C2-6 haloalkenyl, C2-6 alkynyl or C2-6 haloalkynyl;

R3 is hydrogen or cyclobutyl;

R5 is one of the following 5-membered unsaturated heterocyclic ring structures:

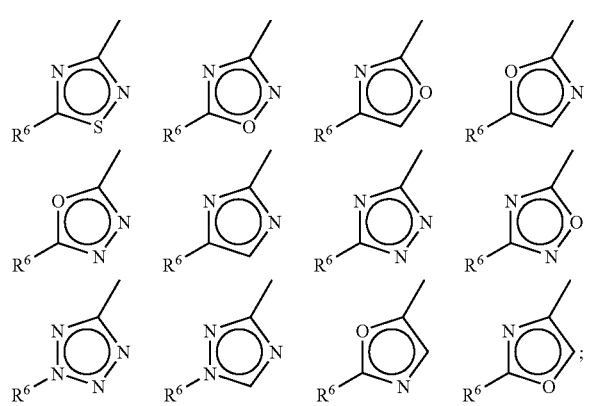

R6 is phenyl, phenylamino substituted by one or more halo, phenylmethyl substituted by one or more halo, or phenethyl substituted by one or more halo; and R8 is hydrogen or a fluoro-substituted phenyl.

3. A compound according to claim 2, wherein

R2 is —CH2—C6H5 or —CH2-heterocyclic aryl each of which may be optionally substituted with one or more of halo, hydroxy, C1-6 alkyl, C1-6 haloalkyl, C1-8 alkoxy, C1-6 haloalkoxy, C2-6 alkenyl, C2-6 haloalkenyl, C2-6 alkynyl or C2-6 haloalkynyl;

R3 is H;

R5 is one of the following 5-membered unsaturated heterocyclic ring structures:

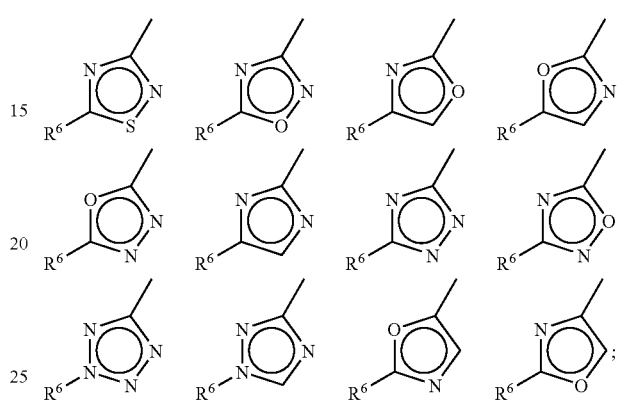

R6 is a meta chloro-substituted phenylamino, a meta chloro-substituted phenylmethy or a meta chloro-substituted phenethyl; and R8 is 3,5-difluorophenyl.

4. A compound according to claim 1, wherein

A is CH;

B is —CH2—;

G is oxygen;

R1 is hydrogen;

R2 is C1-8 alkyl or —CH2-aryl (optionally substituted by one or more of halo, hydroxy, C1-6 alkyl, C1-6 haloalkyl, C1-8 alkoxy, C1-6 haloalkoxy, C2-6 alkenyl, C2-6 haloalkenyl, C2-6 alkynyl or C2-6 haloalkyny);

R3 is cyclobutyl or H, and

R5 is one of the following 5-membered unsaturated heterocyclic ring structures:

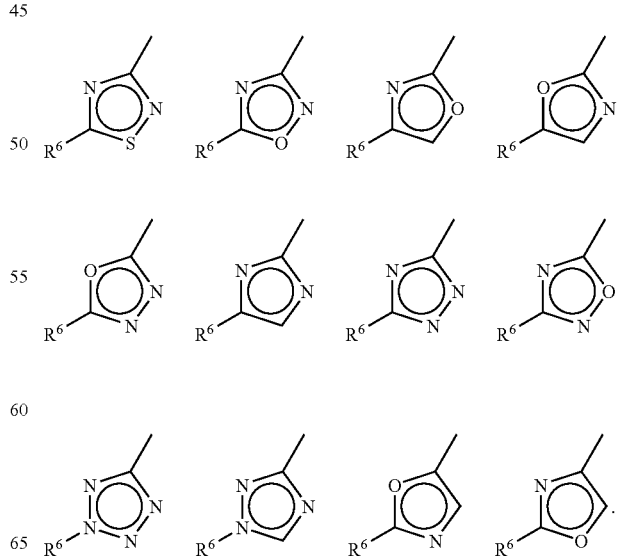

5. A compound according to claim 1, in which A is CH;
B is O;
G is oxygen;
$R_1$ is hydrogen;
$R_2$ is $C_{1-8}$ alkyl, —$CH_2$-aryl (optionally substituted by one or more of halo, hydroxy, $C_{1-6}$ alkyl, $C_{1-6}$ haloalkyl, $C_{1-8}$ alkoxy, $C_{1-6}$ haloalkoxy, $C_{2-6}$ alkenyl, $C_{2-6}$ haloalkenyl, $C_{2-6}$ alkynyl or $C_{2-6}$ haloalkynyl);
$R_3$ is cyclobutyl or H; and
$R_5$ is —$CH_2$—O—$CH_3$, —$CH_2$—O—$CH_2$—$CH_2$—$C_6H_5$ or one of the following 5-membered unsaturated heterocyclic ring structures:

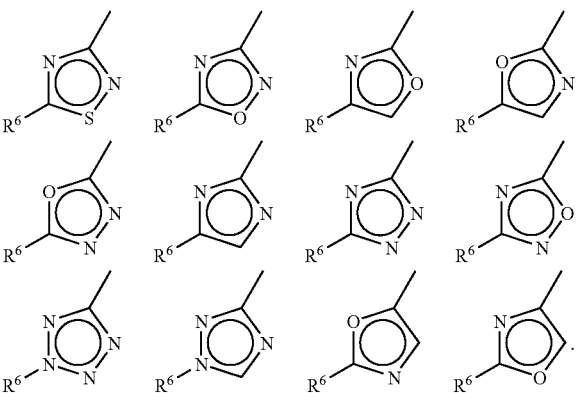

6. A compound according to claim 1, wherein
A is CH; B is NH;
G is oxygen;
$R_1$ is hydrogen;
$R_2$ is $C_{1-8}$ alkyl, —$CH_2$-aryl, a —$CH_2$-heterocyclic group or a —$CH_2$-substituted $C_5$ cycloalkyl (optionally substituted by one or more of halo, hydroxy, $C_{1-6}$ alkyl, $C_{1-6}$ haloalkyl, $C_{1-8}$ alkoxy, $C_{1-6}$ haloalkoxy, $C_{2-6}$ alkenyl, $C_{2-6}$ haloalkenyl, $C_{2-6}$ alkynyl or $C_{2-6}$ haloalkynyl);
$R_3$ is cyclobutyl or H; and
$R_5$ is —$CH_2$—O—$CH_3$, —$CH_2$—O—$CH_2$—$CH_2$—$C_6H_5$ or one of the following 5-membered unsaturated heterocyclic ring structures:

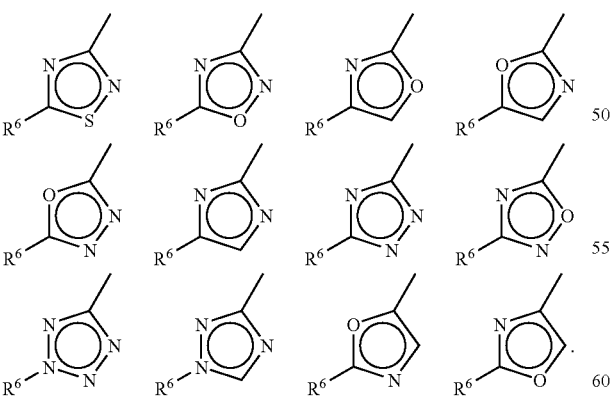

7. A compound according to claim 1, wherein
A is N;
B is —$CH_2$—;
G is oxygen;
$R_1$ is hydrogen;
$R_2$ is $C_{1-8}$ alkyl, —$CH_2$-aryl, a $CH_2$-heterocyclic group or a —$CH_2$-substituted $C_5$ cycloalkyl (optionally substituted one or more of halo, hydroxy, $C_{1-6}$ alkyl, $C_{1-6}$ haloalkyl, $C_{1-8}$ alkoxy, $C_{1-6}$ haloalkoxy, $C_{2-6}$ alkenyl, $C_{2-6}$ haloalkenyl, $C_{2-6}$ alkynyl or $C_{2-6}$ haloalkynyl);
$R_3$ is cyclobutyl or H;
$R_5$ is one of the following 5-membered unsaturated heterocyclic ring structures:

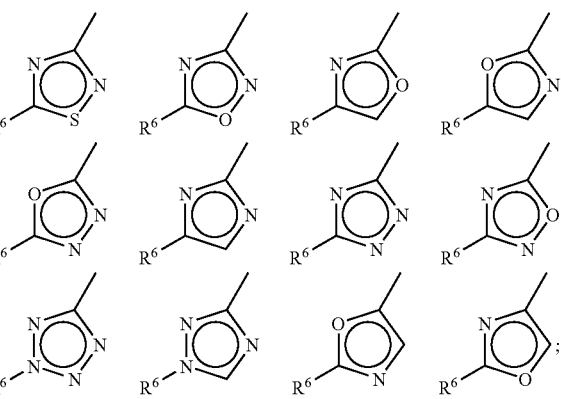

and
$R_8$ is H or phenyl (optionally substituted with halo).

8. A compound according to claim 1, wherein
A is N;
B is —$CH_2$—;
G is oxygen;
$R_1$ is hydrogen;
$R_2$ is $C_{1-8}$ alkyl —$CH_2$-aryl, a —$CH_2$-heterocyclic group or a —$CH_2$-substituted $C_5$ cycloalkyl (optionally substituted by one or more of halo, hydroxy, $C_{1-6}$ alkyl, $C_{1-6}$ haloalky, $C_{1-8}$ alkoxy, $C_{1-6}$ haloalkoxy, $C_{2-6}$ alkenyl, $C_{2-6}$ haloalkenyl, $C_{2-6}$ alkynyl or $C_{2-6}$ haloalkynyl);
$R_3$ is cyclobutyl or H; and
$R_5$ is —$CH_2$—O—$CH_3$.

9. A compound according to claim 1, wherein
A is N;
B is —$CH_2$—;
$R_1$ is hydrogen;
$R_3$ is hydrogen or cyclobutyl;
$R_5$ is one of the following 5-membered unsaturated heterocyclic ring structures:

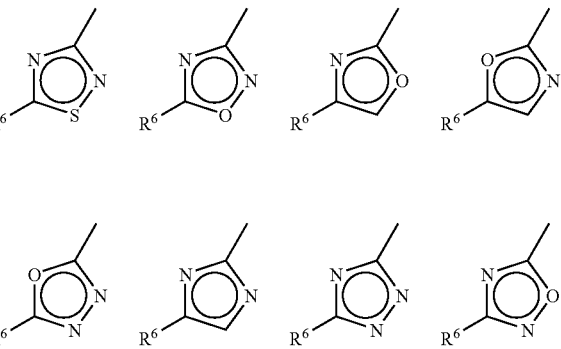

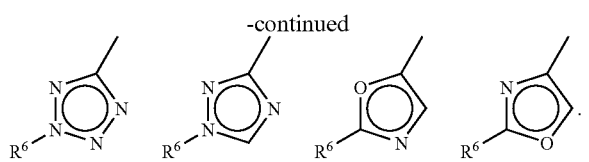

and

R$_8$ is phenyl,3,5-difluorophenyl or H.

10. A compound according to claim 1, having the formula:

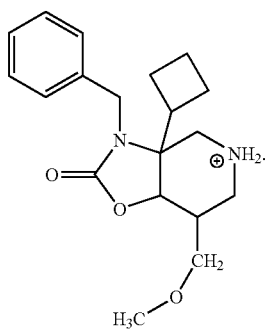

11. A pharmaceutical composition comprising a therapeutically effective amount of the compound of claim 1.

12. A method for the manufacture of a pharmaceutical for the modification an acetylcholine or a muscarinic receptor comprising the step of placing the compound of claim 1 into a pharmaceutical composition in a unit dosage form.

13. The method of claim 12, wherein the pharmaceutical is for the treatment of Alzheimer's disease.

14. A method of modifying a muscarinic acetylcholine receptor or an acetylcholine receptor comprising the administration of a therapeutically effective amount of a compound as claimed in claim 1 to a subject in need thereof.

15. A compound of the formula:

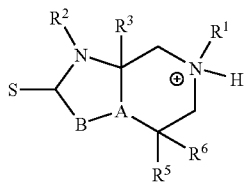

or a pharmaceutically acceptable salt thereof, wherein:

A is CH or nitrogen;

B is —CH$_2$—, —CHF—, —CF$_2$—, NR$_4$ or O, with the proviso that when A is N, B is —CH$_2$—, —CHF— or —CF$_2$—;

G is oxygen or =N—ON,

R$_1$ is hydrogen or C$_{1-6}$ alkyl;

R$_2$ is hydrogen; C$_{1-10}$ alkyl optionally substituted with C$_{1-6}$ alkoxy or halogen; aralkyl, a —CH$_2$-heterocycle or a —CH$_2$—C$_5$ cycloalkyl ring each of which may be optionally substituted with one or more of halo, hydroxyl, C$_{1-6}$ alkyl, C$_{1-6}$ haloalky, C$_{1-8}$ alkoxy, C$_{1-6}$ haloalkoxy, C$_{2-6}$ alkenyl, C$_{2-6}$ haloalkenyl, C$_{2-6}$ alkynyl or C$_{2-6}$ haloalkynyl;

R$_3$ is a cyclic alkyl radical containing from 3-6 carbon atoms or a C$_{1-6}$ alkyl;

R$_4$ is hydrogen or lower alkyl;

R$_5$ is a 5-membered unsaturated heterocyclic ring optionally substituted by a group selected from lower alkyl; arylamino optionally substituted with one or more of halo, hydroxy, C1-6 alkyl, C1-6 haloalkyl, C1-6 alkoxy, C1-6 haloalkoxy, C2-6 alkenyl, C$_{2-6}$ haloalkenyl, C$_{2-6}$ alkynyl or C$_{2-6}$ haloalkynyl; aralkyl optionally substituted with one or more of halo, hydroxy, C$_{1-6}$ alkyl, C$_{1-6}$ haloalkyl, C$_{1-6}$ alkoxy, C$_{1-6}$ haloalkoxy, C$_{2-6}$ alkenyl, C$_{2-6}$ haloalkenyl, C$_{2-6}$ alkynyl or C$_{2-6}$ haloalkynyl; or a group of formula:

wherein n is an integer in the range from 1 to 4 and HET is a heterocyclic group optionally substituted with one or more of halo, hydroxy, C$_{1-6}$ alkyl, C$_{1-6}$ haloalkyl, C$_{1-6}$ alkoxy, C$_{1-6}$ haloalkoxy, C$_{2-6}$ alkenyl, C$_{2-6}$ haloalkenyl, C$_{2-6}$ alkynyl or C$_{2-6}$ haloalkynyl;

or R$_5$ may also be C$_2$-C$_4$-aralkyl, —CH$_2$—O—R$_7$ where R$_7$ is C$_{1-6}$ alkyl, C$_{2-6}$ alkenyl, C$_{2-6}$ alkynyl, C$_2$-C$_4$ aralkyl which groups may be optionally substituted with fluoro or hydroxy; and R$_8$ is hydrogen or aryl (optionally substituted with one or more of halo, hydroxyl, C$_{1-6}$ alkyl, C$_{1-6}$ haloalky, C$_{1-6}$ alkoxy, C$_{1-6}$ haloalkoxy, C$_{2-6}$ alkenyl, C$_{2-6}$ haloalkenyl, C$_{2-6}$ alkynyl or C$_{2-6}$ haloalkynyl);

with the proviso that when either R3 or R8 is not hydrogen, the other is hydrogen.

* * * * *